United States Patent
Clements

(10) Patent No.: US 8,070,744 B1
(45) Date of Patent: Dec. 6, 2011

(54) NASAL ASPIRATION DEVICE

(76) Inventor: Clara C. Clements, Sunnyvale, CA (US)

( * ) Notice: Subject to any disclaimer, the term of this patent is extended or adjusted under 35 U.S.C. 154(b) by 667 days.

(21) Appl. No.: 12/214,822

(22) Filed: Jun. 23, 2008

Related U.S. Application Data

(60) Provisional application No. 61/063,403, filed on Feb. 1, 2008.

(51) Int. Cl.
*A61M 1/00* (2006.01)
(52) U.S. Cl. .................... 604/540; 604/319; 604/315
(58) Field of Classification Search .............. 604/73, 604/173, 315, 319, 540
See application file for complete search history.

(56) References Cited

U.S. PATENT DOCUMENTS

| | | | | |
|---|---|---|---|---|
| 2,644,189 | A * | 7/1953 | Calvin | 15/344 |
| 2,802,260 | A * | 8/1957 | Allen | 30/41.5 |
| 3,653,189 | A * | 4/1972 | Miyake et al. | 55/288 |
| 3,841,840 | A * | 10/1974 | Hundhausen et al. | 422/180 |
| 4,403,611 | A * | 9/1983 | Babbitt et al. | 604/73 |
| 4,684,362 | A * | 8/1987 | Holt | 604/540 |
| 5,114,415 | A * | 5/1992 | Shedlock | 604/319 |
| 6,032,327 | A * | 3/2000 | Oka et al. | 15/346 |
| 6,059,803 | A | 5/2000 | Spilman | |
| 6,135,980 | A | 10/2000 | Vu | |
| 6,471,679 | B1 * | 10/2002 | Suh | 604/319 |
| 6,517,511 | B2 | 2/2003 | Yao | |
| 6,595,949 | B1 * | 7/2003 | Shapiro | 604/73 |
| 6,991,638 | B2 * | 1/2006 | Wang | 606/162 |
| 2002/0095112 | A1 * | 7/2002 | Hamdan | 604/11 |
| 2003/0109854 | A1 * | 6/2003 | Chen | 604/540 |
| 2006/0241565 | A1 * | 10/2006 | Chiou | 604/540 |
| 2008/0208112 | A1 * | 8/2008 | Bensoussan | 604/35 |
| 2009/0048581 | A1 * | 2/2009 | Sebban | 604/540 |
| 2009/0105674 | A1 * | 4/2009 | Cheng | 604/320 |
| 2010/0168690 | A1 * | 7/2010 | Bensoussan | 604/319 |

FOREIGN PATENT DOCUMENTS

| | | | |
|---|---|---|---|
| CA | 1136018 | * | 11/1982 |
| EP | 1051984 A2 | * | 11/2000 |

* cited by examiner

*Primary Examiner* — Melanie Hand
*Assistant Examiner* — Paula Craig
(74) *Attorney, Agent, or Firm* — Emery L. Tracy

(57) ABSTRACT

A nasal aspiration device for clearing nasal passages is provided. The nasal aspiration device comprises a housing having a proximal end and a distal end. A plurality of slots are formed in the proximal end of the housing. A fan is mounted within the housing and a power mechanism powers the fan. An activation mechanism activates the power means. A nose cone is removably connectable to the distal end of the housing, the nose cone having an opening wherein upon powering the fan, air travels into the opening in the nose cone, through the housing, and out of the housing the slots.

9 Claims, 1 Drawing Sheet

NASAL ASPIRATION DEVICE

The present application claims benefit of priority of pending provisional patent application Ser. No. 61/063,403, filed on Feb. 1, 2008, entitled "Nasal Aspiration Device".

BACKGROUND OF THE INVENTION

1. Field of the Invention

This invention relates generally to a nasal aspiration device and, more particularly, the invention relates to a nasal aspiration device featuring a battery operated nasal respirator that facilitates a more comfortable and sanitary method of clearing nasal passages.

2. Description of the Prior Art

Helping infants and toddlers less than four years old clear a stuffy nose is a difficult challenge for most parents. Babies cannot blow their noses at all, and small children rarely blow their noses with the force to properly clear their nasal passages (they are still very young, after all). Parents are constantly wiping runny noses with tissues, and then continually administering medicines to stop the flow of mucus generated by colds.

To help clear clogged nasal passages in infants and children, parents typically use a manual nasal aspirator. Basic in design, these instruments essentially consist of a tapered insertion tube connected to a bulbous squeeze apparatus. As such, a parent need only insert the tube into a child's nostril, and repeatedly squeeze the bulb to create suction action. The mucus is then transferred from the child into the aspirator, and the unit is emptied by squeezing out the mucus into a trash container. As can be imagined, these manual devices present more than a fair share of challenges. Particularly, this method of clearing a child's nose is hardly sanitary, resulting in extremely unpleasant messes. Additionally, the design of the manual aspirator can be very uncomfortable for the child, resulting in a screaming, squirming baby who makes it even more difficult to complete the task.

SUMMARY

The present invention is a nasal aspiration device for clearing nasal passages. The nasal aspiration device comprises a housing having a proximal end and a distal end. A plurality of slots are formed in the proximal end of the housing. A fan is mounted within the housing and a power mechanism powers the fan. An activation mechanism activates the power means. A nose cone is removably connectable to the distal end of the housing, the nose cone having an opening wherein upon powering the fan, air travels into the opening in the nose cone, through the housing, and out of the housing the slots.

The present invention further includes a method for clearing nasal passages. The method comprises providing a housing having a proximal end and a distal end, forming a plurality of slots in the proximal end of the housing, mounting a fan within the housing, removably connecting a nose cone to the distal end of the housing, forming an opening in the nose cone, powering the fan, drawing air into the opening in the nose cone, directing the air through the housing, and directing the air out of the housing through the slots.

DETAILED DESCRIPTION OF THE PREFERRED EMBODIMENTS

Figure 1:
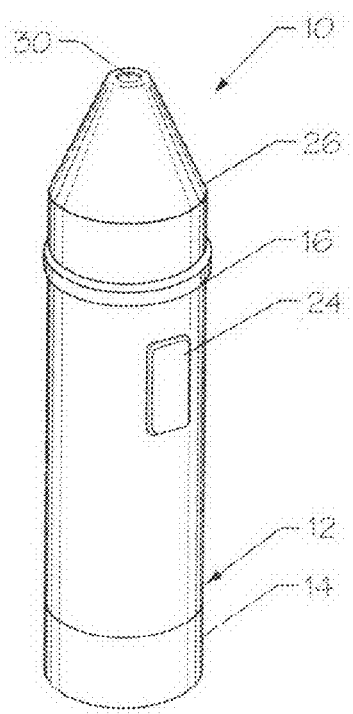
FIG. 1 is a perspective view illustrating a nasal aspiration device, constructed in accordance with the present invention.
Figure 2:
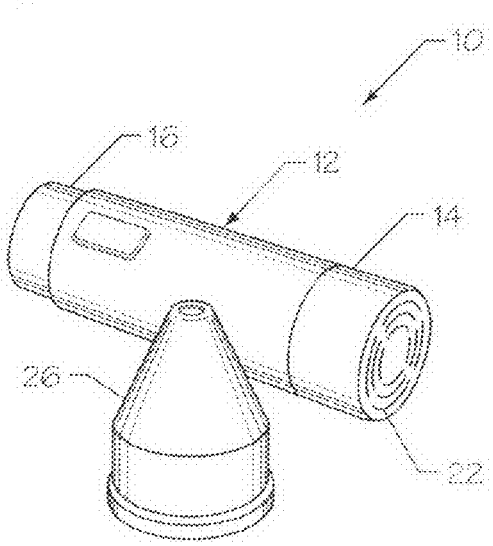
FIG. 2 is a perspective view illustrating the nasal aspiration device of FIG. 1, constructed in accordance with the present invention, with the nose cone removed from the housing.
Figure 3:
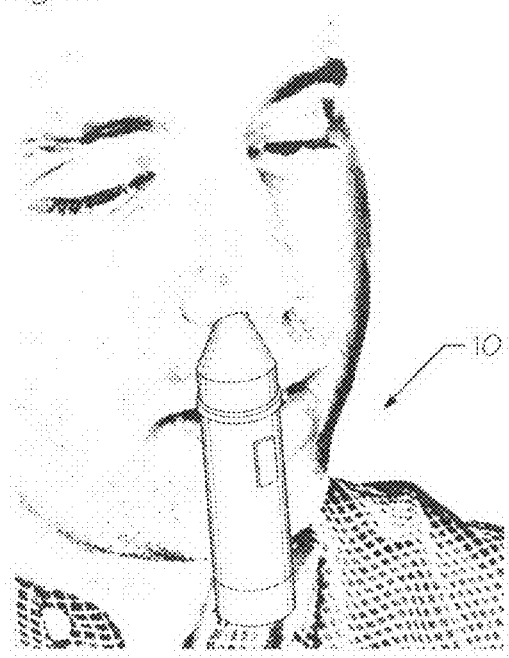
FIG. 3 is a perspective view illustrating the nasal aspiration device, constructed in accordance with the present invention, with the device in use.
Figure 4:
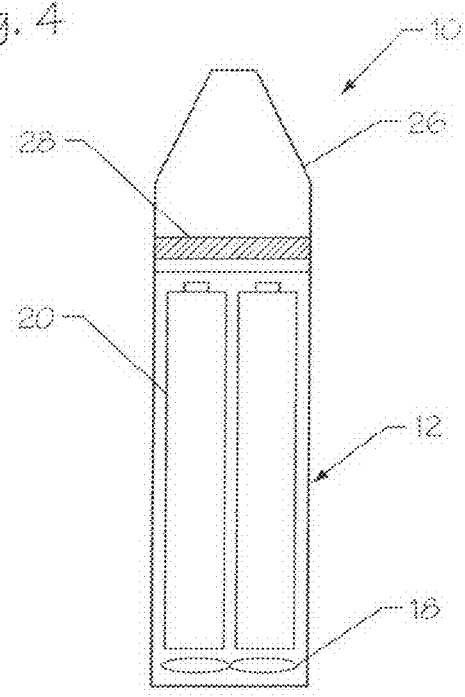
FIG. 4 is a sectional side view illustrating the nasal aspiration device, constructed in accordance with the present invention.

As illustrated in FIGS. 1-4, the present invention is a nasal aspiration device, indicated generally at 10, for clearing nasal passages. Simply stated, the nasal aspiration device 10 of the present invention is a battery operated nasal respirator facilitating a more comfortable and sanitary method of clearing nasal passages.

The nasal aspiration device 10 of the present invention includes a slim lined, substantially cylindrical shaped housing 12 having a proximal end 14 and a distal end 16. Preferably, the housing 12 of the nasal aspiration device 10 is constructed from a durable plastic material and measures approximately five (5") inches in length. It should be noted that while the housing 12 has been described as being constructed from a certain material and having a certain length, it is within the scope of the present invention for the housing 12 to be constructed from a variety of materials and having any preferred length.

Internally contained within the proximal end 14 of the housing 12 of the nasal aspiration device 10 of the present invention is a small, fan-like component 18 providing suction power for the nasal aspiration device 10. Extending downward, the interior of the middle of the nasal aspiration device 10, between the proximal end 14 and the distal end 16, houses power means such as one or two, AAA alkaline batteries 20 for powering the fan of the nasal aspiration device 10. A plurality of slots or apertures 22 are provided in the proximal end 14 for forcing air into the distal end 16 and out of the proximal end 14, as will be described in further detail below. An activation button or switch 24 is provided on the housing 12 for turning the fan of the nasal aspiration device 10 on and off.

The distal end 16 of the nasal aspiration device 10 of the present invention contains a removable, tapered nose cone 26 containing a disposable filter or filtering system 28. The nose cone 26 has an opening 30 for receiving mucous and other debris from the nasal passages of the user. Use and operation of the nasal aspiration device 10 will be described in further detail below.

The manner of use of the nasal aspiration device 10 of the present invention will now be described. It will be understood by those skilled in the art that the manner of use of the nasal aspiration device 10 described herein is merely one method of use and other methods of use of the nasal aspiration device 10 are within the scope of the present invention.

The nasal aspiration device 10 of the present invention is extremely easy to use. First, the tapered nose cone 26 at the distal end 16 of the housing 12 of the nasal aspiration device 10 is placed at the entrance of a nostril, but not completely inside. Powering the nasal aspiration device 10 with the activation button 24, the parent need only hold the nasal aspiration device 10 in place as it works. The fan unit 18 provides the suction power and as the mucus enters the opening 30 or ingress point of the nose cone 26, the disposable filter 28 works to capture the mucus. When finished, the parent simply twists off the nose cone 26 at the distal end 16 of the housing 12 of the nasal aspiration device 10, disposes of the filter 28, and replaces the filter 28 with another clean filter. In this manner, the mucus residue can be conveniently disposed without messy, unsanitary contact.

The lightweight design and plastic composition of the nasal aspiration device 10 of the present invention is sturdy, and very easy to use and clean. Completely safe and comfortable for the child, the tapered nose cone 26 fits against the child's nostril without entering the nasal canal, thereby rendering the suctioning endeavor less terrifying for the child. As such, the clearing of the nasal passages can be completed in an expedient and easy manner. By keeping a child's nose clear of bacteria and mucus, further infection and illness can be prevented, a positive step for both the parent and the child. Furthermore, the nasal aspiration device 10 can also help care for elderly and disabled persons, with larger devices employed for these patients who are unable to clear their nasal passages on their own.

In summary, the nasal aspiration device 10 of the present invention is a clean, safe, and effective way to help your young child clear a stuffy nose. Most importantly, such efficient clearing of the nose will help prevent further infection, discomfort, and perhaps a trip to the doctor. Fully developed, the nasal aspiration device 10 will be received by the vast majority of parents with young children, as well as those charged with caring for adults who are disabled.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. A nasal aspiration device for clearing nasal passages, the nasal aspiration device comprising:
   a housing having a proximal end and a distal end;
   a plurality of slots formed in the proximal end of the housing;
   a fan mounted in the proximal end of the housing, the fan having a propeller rotatably mounted directly adjacent the slots;
   power means for powering the fan;
   activation means for activating the power means; and
   a nose cone removably connectable to the distal end of the housing, the nose cone having an opening;
   wherein upon powering the fan, air travels into the opening in the nose cone, through the housing, and out of the housing through the slots; and
   wherein the power means are batteries, and the batteries are releasably mounted between the nose cone and the fan.

2. The nasal aspiration device of claim 1 wherein the housing is substantially cylindrical shaped.

3. The nasal aspiration device of claim 1 wherein the housing is constructed from a plastic material and measures approximately five (5") inches in length.

4. The nasal aspiration device of claim 1 wherein the activation means is an activation button on the housing.

5. The nasal aspiration device of claim 1 wherein the nose cone is tapered.

6. The nasal aspiration device of claim 1 and further comprising:
   a removable, disposable filter within the nose cone.

7. A nasal aspiration device for clearing nasal passages, the nasal aspiration device comprising:
   a housing having a proximal end and a distal end;
   a plurality of slots formed in the proximal end of the housing;
   a fan mounted within the housing and at the proximal end of the housing, the fan having a propeller mounted directly adjacent the slots;
   power means for powering the fan;
   activation means for activating the power means;
   a tapered nose cone removably connectable to the distal end of the housing, the nose cone having an opening; and
   a removable, disposable filter within the nose cone;
   wherein upon powering the fan, air travels into the opening in the nose cone, through the housing, and out of the housing through the slots; and
   wherein the power means are batteries, and the batteries are releasably mounted between the nose cone and the fan.

8. The nasal aspiration device of claim 7 wherein the housing is substantially cylindrical shaped.

9. The nasal aspiration device of claim 7 wherein the activation means is an activation button on the housing.

* * * * *